United States Patent [19]
Heiba

[11] 4,452,629
[45] Jun. 5, 1984

[54] HERBICIDAL N,N'-THIO-5(SUBSTITUTED-PHENOXY OR -PYRIDYLOXY)-2-SUBSTITUTED BENZOIC ACID SULFONAMIDES AND SULFAMIDOYL FLUORIDE

[76] Inventor: El-Ahmadi I. Heiba, 11 Balsam La., Princeton, N.J. 08540

[21] Appl. No.: 409,615

[22] Filed: Aug. 19, 1982

[51] Int. Cl.$^3$ .............................................. E05B 63/00
[52] U.S. Cl. ..................................... 71/103; 546/297; 546/303; 560/12; 560/13; 562/430; 260/465 D; 564/80
[58] Field of Search ............. 71/103; 564/80; 560/12, 560/13; 546/297, 303; 260/465 D; 562/430

[56] References Cited

U.S. PATENT DOCUMENTS 3,282,991  11/1966  Klein et al. ........................ 260/501
4,285,723   8/1981  Cartwright ........................... 71/103

Primary Examiner—Paul J. Killos
Attorney, Agent, or Firm—Sixbey, Friedman & Leedom

[57] ABSTRACT

N,N'(thio)-5(substituted-phenoxy or pyridyloxy)-2-substituted benzoic acid sulphonamide and sulfamidoyl fluoride their preparation and use as herbicides are disclosed.

9 Claims, No Drawings

HERBICIDAL N,N'-THIO-5(SUBSTITUTED-PHENOXY OR -PYRIDYLOXY)-2-SUBSTITUTED BENZOIC ACID SULFONAMIDES AND SULFAMIDOYL FLUORIDE

BACKGROUND OF THE INVENTION

Herbicidal 5-(2-chloro-4-trifluoromethyl)-phenoxy-2-nitrobenzoic acid and salts thereof, and various herbicidal derivatives of these compounds have been proposed including alkyl and cycloalkyl esters, alkylthio esters, phenyl ester, alkyl and dialkyl amido and benzoyl chloride forms. U.S. Patents which describe such compounds and the like include Nos. 3,652,645; 3,784,635; 3,873,302; 3,983,168; 3,907,866; 3,798,276; 3,928,416; and 4,063,929. Published European Applications 3416 and 23,292 disclose N-sulphonyl-3-phenoxybenzamide derivatives and their salts are herbicides.

SUMMARY OF THE INVENTION

This invention provides certain herbicidal compounds of the formula:

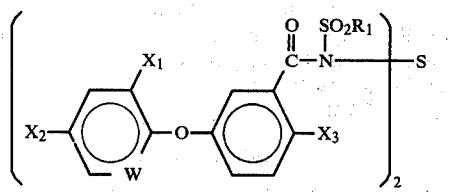   I wherein $R_1$ is F; substituted or unsubstituted hydrocarbyl; (e.g., having from 1 to 12 carbon atoms), substituted or unsubstituted phenyl; or substituted or unsubstituted heterocycle, (e.g., having from 5 to 7 ring atoms).

Examples of $R_1$ include $C_1$–$C_4$ alkyl; $C_1$–$C_4$ alkyl substituted with one or more, preferably no more than 4, of aryl, (particularly phenyl), Cl, Br, OH, O alkyl ($C_1$–$C_4$), SH, S alkyl ($C_1$–$C_4$), COOH, COO alkyl ($C_2$–$C_5$), CN, etc.; $C_2$–$C_6$ alkenyl; $C_2$–$C_6$ alkynyl; and aryl, particularly phenyl; or aryl substituted with one or more, preferably no more than 4, of Cl, Br, alkyl ($C_1$–$C_4$), CN, COOH, COO alkyl ($C_2$–$C_5$), $NO_2$, OH, O alkyl ($C_1$–$C_4$), SH, S alkyl ($C_1$–$C_4$), etc.;

W is CH, C—$X_4$ or N;

$X_1$, $X_2$, $X_3$ and $X_4$, are substituents capable of imparting herbicidal properties. Suitable substituents include halogen, such as F, Cl, and Br; polyhaloakyl, such as $CF_3$; $NO_2$; CN; alkyl; alkoxy; $SO_2$ alkyl; $SO_2NH_2$; NO; COO alkyl and the like in which the alkyl and alkoxy groups preferably contain 1 to 4 carbon atoms.

Compounds in which $X_1$ is Cl, $X_2$ is $CF_3$ and W is CH are preferred.

An exemplary compound has the Formula I in which $X_1$ is Cl, $X_2$ is $CF_3$, $X_3$ is $NO_2$, W is CH, and $R_1$ is methyl. Another exemplary compound with excellent systemic herbicidal activity has the Formula I in which $X_1$ is Cl, $X_2$ is $CF_3$, $X_3$ is $NO_2$, W is CH, and $R_1$ is fluorine.

The compounds of this invention can be easily prepared from appropriate precursor by methods known in the art although it is believed that these methods have not previously been applied to make compounds of the present invention. Precursors in which $R_1$ is other than F and S in the above formula is hydrogen and the sodium salt thereof are known and are described in European Published Application Nos. 3416 and 23, 392 which are incorporated herein by reference in their entirety. The precursors having Formula II in which $R_1$ is

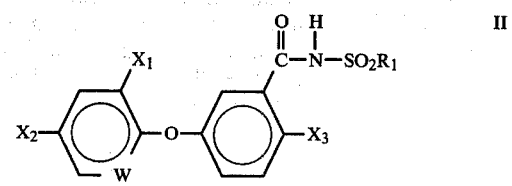   II other than F can be prepared in good yields by reacting the appropriate aryloxyl benzoic acid chloride with the corresponding sulfonamide such as $CH_3SO_2NH_2$, $CH_3CH_2SO_2NH_2$, $CF_3SO_2NH_2$, $ClCH_2SO_2NH_2$, $ClCF_2SO_2NH_2$, $Cl_3CSO_2NH_2$, phenyl sulfonamide and substituted phenyl sulfonamide. The reaction can be conducted by heating the reactants in the temperature ranges 50°–200°, preferably between 110°–150°. The reaction can be affected by heating the mixed reactants per se or in inreactive solvents for example chlorobenzne, toluene and dichlorobenzene and the like. High yields of the precursors having formula II can be obtained by conducting the above mentioned reaction in the absence of an acid acceptor, although in certain instances it might be desirable to use one mole equivalent of an acid acceptor such as pyridene, quinoline, trimethyl amine, triethylamine and the like. The precursors having formula II can be separated and purified by usual methods known to those skilled in the art.

The precursors having formula II in which $R_1$ is F can be prepared in the known manner by reacting the appropriate aryloxyl benzoic acid chloride with the known amidosulfuryl fluoride $NH_2SO_2F$. The reaction can be advantageously conducted by heating the reactants in the temperature ranges of 50°–150° till hydrogen chloride ceases to evolve. The reaction can be conducted by heating the mixed reactants per se or in inreactive solvents for example chlorobenzene, dichlorobenzene, dichloromethane and the like.

Another useful method which can be used to prepare the precursors having Formula II in which $R_1$ is F and that is to react the appropriate aryloxyl benzoic acid amide with oxalyl chloride to form the corresponding carbonyl isocyanate i.e. compounds having the

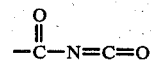

moiety attached adjacent to $X_3$ in the diphenylether nucleus in Formula II. The carbonyl isocyanate precursors prepared in the above described and known manner are then reacted with fluorosulfuric acid HO—$SO_2F$ to yield the corresponding sulfamidoyl fluoride of Formula II in which $R_1$ is F. The overall reaction sequences may be illustrated as follows:

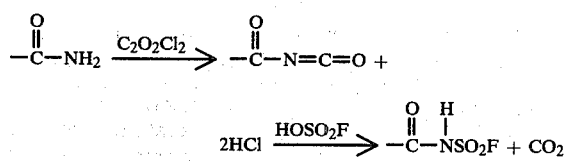

The compounds of this invention having Formula I can be easily prepared by any of the following methods:

(1) By the reaction of the alkali cation form of the precursors having Formula II with one half mole equivalent of sulfur dichloride in a solvent such as tetrahydrofuran, dialkylethers and the like. The preferred alkali cation are those of alkali metal such as K or Na but ammonium or substituted ammonium cation can also be used. The above mentioned reaction is usually completed after 6–48 hours depending on the reaction temperatures. Those reactions are illustrated as:

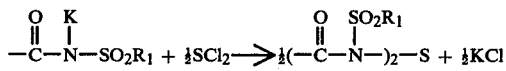

(2) By the reaction of the N-halo-derivative (particularly chloro) of the precursors having Formula II with one half mole equivalent of potassium or sodium sulfide in a solvent such as tetrahydrofuran, dialkyl ethers and the like. The N-chloro-derivative of compounds of Formula II can be easily prepared by methods known in the art involving the direct N-chlorination of the appropriate compound of Formula II with either sodium hypochloride, hypochlorous acid or t-BuOCl. Another useful method to prepare the N-chloro-derivatives of compounds of formula II is by reacting the appropriate aryloxyl benzoic acid chloride with the appropriate N-chloro-N-sodiosulfonamides NaNCl—$SO_2R_1$ which can be prepared by the method of F.E.

Hardy, Journal Chemical Society (c) 2087(1970). The compounds of this invention can be advantageously employed as herbicides and various crops for example, soybeans, cotton and peanuts. They can be applied per se, but may be applied as the toxic components in pesticidal compositions of the compound and a carrier. These compositions may be applied directly to the soil and often incorporated therewith. The compositions can be applied as granulars or dusts; as liquid sprays, or as gas-propelled sprays and can contain, in addition to a carrier, additives such as emulsifying agents, binding agents gases compressed to the liquid state, odorants, stabilizers, and the like. A wide variety of liquid and solid carriers including talc, bentonite, diatomaceous earth pyrophyllite, fullers earth, gypsum, flours derived from cotton seeds and nut shells, and various natural and synthetic clays having a pH not exceeding about 9.5. Non-limiting examples of liquid carriers include water, organic solvents such as alcohols, ketones, light oils, and medium oils and vegetable oils such as cottonseed oil. In practice herbicidal application is measured in terms of pounds of herbicide applied per acre. The compounds of this invention are effective herbicides when applied in herbicidal amounts, e.g., at rates between about 0.03 pound and about 10 pounds per acre.

EXAMPLE 1

Preparation of
N,N'-thio-5-(2-chloro-4-trifluoromethyl)-phenoxy-2-nitro-N-methanesulfonyl benzamide (formula I wherein $R_1$ is methyl, $X_2$ is $CF_3$, $X_1$ is Cl, W is CH and $X_3$ is $NO_2$)

The corresponding amide of Formula II, m.p. 218°, 0.05 mole was dissolved in 100 ml. anhydrous tetrahydrofuran and 0.05 mole potassium tert-butoxide was added while stirring at room temperature. Sulfur dichloride, 0.015 mole, was added to the reaction mixture and stirring was continued for 48 hours. The reaction mixture was diluted with cold water and the precipitate was washed with 10 percent sodium carbonate solution, to remove unreacted starting material, filtered and air dried. The dried solid was crystallized from hot ethanol to yield crystals m.p. 173°–174°, (yield was 75% of theory). The product is stable at pH 10 but liberates colloidal sulfur upon the addition of hydrochloric acid.

EXAMPLE 2

The N,N'-thio compound of example 1 was also prepared by reacting a chloroform/ether solution of N-chloro-5-(2-chloro-4-trifluoromethyl)-phenoxy-2-nitro-N-methanesulfonyl benzamide, m.p. 161° with potassium sulfide while stirring at room temperature for 72 hours. The reaction mixture was worked out as in example 1 to yield crystals m.p. 172°–177°, mixed m.p. 173°–178° with the crystals from example 1.

EXAMPLES OF APPLICATION

EXAMPLE 3

A wettable powder easily dispersible in water is obtained by mixing 25 parts by weight of N,N'-thio-5-(2-chloro-4-trifluoromethyl)-phenoxy-2-nitro-N-methanesulfonyl benzamide as active ingredient, 64 parts by weight of kaolin containing quartz as inert substance, 10 parts by weight of potassium salt of ligninsulfonic acid, 1 part by weight of sodium salt of oleymethyltaurine as wetting and dispersing agent and by grinding it.

EXAMPLE 4

A mixture of weeds and some crop plants were sown in vessels having a dimension of 29×22×6 cm. charged with earth, and the seeds were covered with earth. The same day the herbicidal composition, cited in Example 3, which was emulsified in water, was sprayed on the surface of the soil. The vessels were kept outdoors, during the summer growing season. Three weeks after treatment, the following results were obtained, expressed as degree of damage in present (100=complete kill, 0=no damage).

| Dosage, lb/acre (active ingredient) | 0.5 | 0.25 |
|---|---|---|
| Grass weeds | | |
| Barnyard grass | 100. | 80. |
| Crab grass | 80. | 70. |
| Broadleaf weeds | | |
| Velvet leaf | 100. | 90. |
| Cocklebur | 100. | 80. |
| Morning glory | 70. | 60. |
| Crop plants | | |
| Cotton | 10. | 0. |
| Soybean | 0. | 0. |

The results show that the product according to this invention has very good herbicidal activity against broad-leaf weeds and grass weeds. Simultaneously, there is excellent preserving effect for the crop plants, soybean and cotton.

EXAMPLE 5

An emulsifiable concentrate is composed of 10 parts by weight of N,N'-thio-5-(2-chloro-4-trifluoromethyl)-phenoxy-2-nitro-N-methanesulfonyl benzamide, 80 parts by weight of dichloromethane as solvent, and 10 parts by weight of nonylphenol (10EO) as emulsifier.

EXAMPLE 6

A mixture of weeds and some crops were sown in vessels having a diameter of 29×22×6 cm. charged with earth and the seeds were covered with earth. The vessels were watered and kept outdoors during the Summer Growing Season. One week after the crop plants and the weeds had emerged, the herbicidal composition cited in Example 5, which was emulsified in water, was sprayed in such a way that the crop and weed plants were fully wetted. Two weeks after the treatment, the following results were obtained, expressed as degree of damage in percent.

| Dosage, lb/acre (active ingredient) | 0.5 | 0.25 |
|---|---|---|
| *Grass weeds* | | |
| Barnyard grass | 70. | 60. |
| Crab grass | 80. | 50. |
| *Broadleaf weeds* | | |
| Velvet leaf | 100. | 90. |
| Cocklebur | 100. | 100. |
| Morning glory | 90. | 90. |
| *Crop plants* | | |
| Cotton | 0. | 10. |
| Soybean | 0. | 0. |

The results show that the product according to this invention has a very good herbicidal activity, when applied in a post-emergence application against broadleaf and grass weeds while simultaneously has excellent preserving effect for crop plants, soybean and cotton.

Although the present invention has been described with preferred embodiments, it is to be understood that modifications and variations may be resorted to, without departing from the spirit and scope of this invention, as those skilled in the art will readily understand. Such modifications are considered to be within the purview and scope of the appended claims.

I claim:

1. A compound having herbicidal activity of the formula

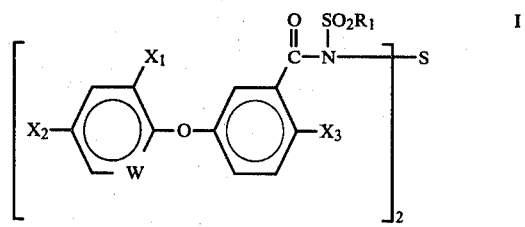

wherein $R_1$ is F; a $C_1$-$C_4$ alkyl group optionally substituted by one or more halogen atoms; or a phenyl group optionally substituted by one or more halogen atoms;

W is CH, C-halogen or N;

$X_1$, $X_2$ and $X_3$ are each a halogen atom, a $C_1$-$C_4$ alkyl group, a trifluoromethyl group, a nitro group or a cyano group.

2. A compound as claimed in claim 1 wherein the halogen atom optionally substituted in $C_1$-$C_4$ alkyl and phenyl in the definition of $R_1$ is chlorine or bromine.

3. A compound as claimed in claim 1 wherein $X_1$ is Cl; $X_2$ is $CF_3$; and W is CH.

4. A compound as claimed in claim 3 wherein $X_3$ is $NO_2$.

5. A compound as claimed in claim 4 wherein $R_1$ is fluorine.

6. A compound as claimed in claim 4 wherein $R_1$ is an unsubstituted $C_1$-$C_4$ alkyl group.

7. A compound as claimed in claim 4 wherein $R_1$ is methyl.

8. A herbicidal composition comprising a compound according to claim 1 and an agronomically acceptable carrier.

9. A method of combating unwanted plants which comprising contacting them with a herbicidally effective amount of a compound according to claim 1.

* * * * *